United States Patent [19]

Kubofcik

[11] Patent Number: 5,038,929

[45] Date of Patent: Aug. 13, 1991

[54] SHARPS DISPOSAL SYSTEM

[76] Inventor: Susanne Kubofcik, 6 Quail Ct., Shelton, Conn. 06484

[21] Appl. No.: 534,469

[22] Filed: Jun. 7, 1990

[51] Int. Cl.⁵ .................... B65D 81/00; B65B 23/00; B29G 67/00

[52] U.S. Cl. .................... 206/210; 206/523; 206/524; 206/364; 206/365; 206/366; 206/337; 206/459; 264/46.6; 53/472

[58] Field of Search ............... 206/205, 210, 523, 524, 206/364, 365, 366, 370; 264/46.6, 46.7; 53/472

[56] References Cited

U.S. PATENT DOCUMENTS

| | | | |
|---|---|---|---|
| 2,557,222 | 6/1951 | Goode | 206/365 |
| 3,204,385 | 9/1965 | Remer et al. | 206/524 X |
| 3,388,195 | 6/1968 | Christenson | 206/524 X |
| 4,050,894 | 9/1977 | Genis | 206/365 X |
| 4,182,448 | 1/1986 | Hack et al. | 206/365 X |
| 4,446,967 | 5/1984 | Halkyard | 206/365 X |
| 4,813,538 | 3/1989 | Blackman | 206/205 X |

Primary Examiner—William I. Price
Attorney, Agent, or Firm—Parmelee, Bollinger & Bramblett

[57] ABSTRACT

A disposal system for sharp instruments comprises a rectangular container, and a plurality of elongated aligned receptacles therein for receiving sharp instruments. The receptacles each comprise a puncture resistant casing defining an entry opening, a rupturable seal deployed over the entry opening and a curable liquid contained within the casing and seal, said liquid being curable to a hardened state upon rupture of the seal. A lid pivots over the seal prior to use, and one or more of the containers is positionable on a wall bracket. A sharp instrument is inserted through the rupturable seal and immersed in the liquid within the receptacle, whereupon the liquid hardens and encases the instrument. The seal is provided with ascending numbers, respectively positioned over the entry openings, to provide a count of receptacles which have been used.

24 Claims, 2 Drawing Sheets

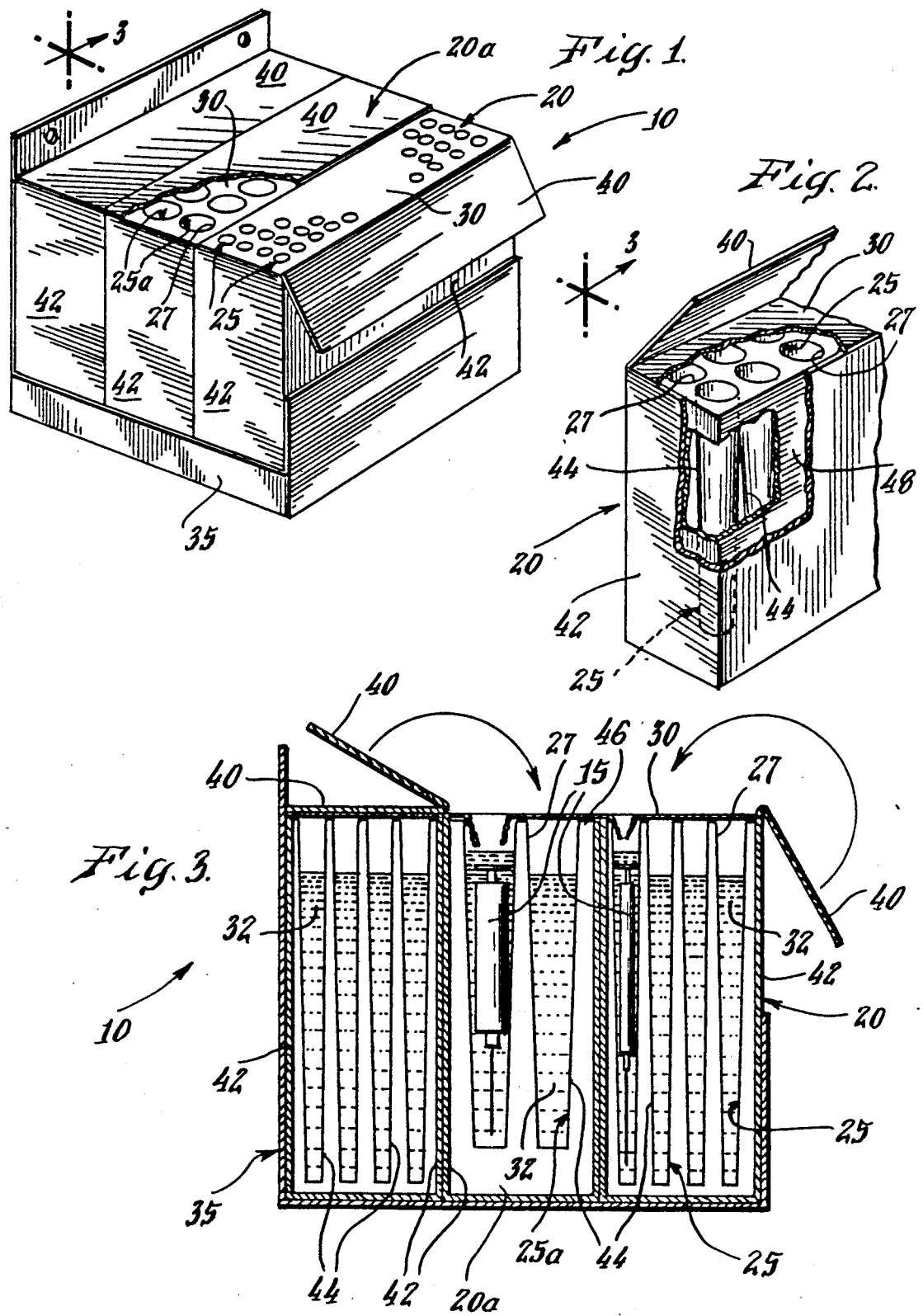

SHARPS DISPOSAL SYSTEM

FIELD OF INVENTION

This invention relates to a system for the safe and accountable disposal of biologically contaminated sharp instruments, such as syringes.

BACKGROUND OF INVENTION

The safe and accountable disposal of biologically contaminated sharp instruments is of great concern to medical and public health personnel. Such instruments are sometimes referred to by the shortened "sharps". This concern is caused by the presence of AIDS and other serious, communicable diseases in patients being treated, and the possibility that such diseases could be transmitted to medical personnel in the treatment area or to others handling contaminated materials from the treatment area. The problem is particularly acute with respect to sharp instruments, such as syringes, in that AIDS and other diseases can be communicated through breaks in the skin. The problem is exacerbated by drug abusers, who are known to salvage and reuse syringes without due regard to the possible consequences.

Accordingly, there is a need for disposal systems which provide for the immediate security of contaminated sharps, preferably also accounting for the number of sharps in the treatment area, and also providing for long term security of the sharps during storage, transport and ultimate disposal.

The products now available for disposal of sharps generally comprise a container having a restricted opening thereto, whereby the sharps are inserted through the restricted opening and confined within the container. The opening may be protected by a spring biased door and the container itself is generally designed to be unopenable or at least difficult to open. The containers are generally constructed of polypropylene, and may be autoclaved and incinerated.

There are weaknesses in the present disposal system. A primary weakness is that there is no accountability for the number of sharps, i.e., it is not readily apparent how many sharps have been inserted into a container for disposal. Further, since the openings are operable during the time the containers are filled and taken away, there is the possibility of unauthorized retrieval of the sharps through the openings, or of opening a container by force to remove the sharps. No provision is made for diminishing the infectious nature of the sharps, which remain dangerous at least through the time of autoclaving or incineration. A step such as autoclaving or incineration is therefor absolutely necessary in the disposal process.

SUMMARY OF THE INVENTION

Accordingly, it is a principal object of the invention herein to provide a system for the safe and accountable disposal of biologically contaminated sharps.

It is a further object of the invention herein to provide a sharps disposal system which isolates and individually secures each sharp at the area of use.

It is an additional object of the invention herein to provide a sharps disposal system which exhibits a count of the number of sharps isolated and secured therein.

It is also an object of the invention herein to provide a sharps disposal system which isolates and secures sharps from the time of use to final disposal.

A disposal system for biologically contaminated sharp instruments (sharps) such as syringes comprises a receptacle having a puncture resistant casing defining an entry opening thereto and a rupturable seal deployed over the entry opening. A viscous curable liquid is contained within the casing and sealed, said liquid being curable to a hardened state upon breaking of the seal. A sharp instrument may be pushed through the seal into the viscous liquid within the receptacle, and the liquid thereafter hardens about the sharp instrument, thereby isolating it, protecting it from contact with medical personnel or from unauthorized further use, and giving visual indication, via the ruptured seal, of disposal.

According to other aspects of the invention, the liquid may be a resin which is air-curable at room temperatures. The liquid is also treated with germicides and the like to prevent propagation of contaminants within the disposal system.

According to additional aspects of the invention, a plurality of elongated receptacles are aligned in one container. The rupturable seal is a foil covering the entry openings to the receptacles, and sequential numbers are printed on the respective openings. This provides for disposing of a plurality of sharps in one container and for quickly ascertaining a count of the number of sharps the container has received.

Other and more specific objects and features of the invention herein will appear in the following description of the preferred embodiment and the claims, taken together with the drawings.

DRAWINGS

FIG. 1 is a perspective view of a sharps disposal system according to the invention herein, including three containers and a wall mounting bracket;

FIG. 2 is a perspective view, partially cut away, of one of the containers of FIG. 1;

FIG. 3 is a side elevation view, partially cut away and in section, of the sharps disposal system of FIG. 1;

The same reference numerals refer to the same elements throughout the various figures.

DESCRIPTION OF PREFERRED EMBODIMENT

Figure 4:
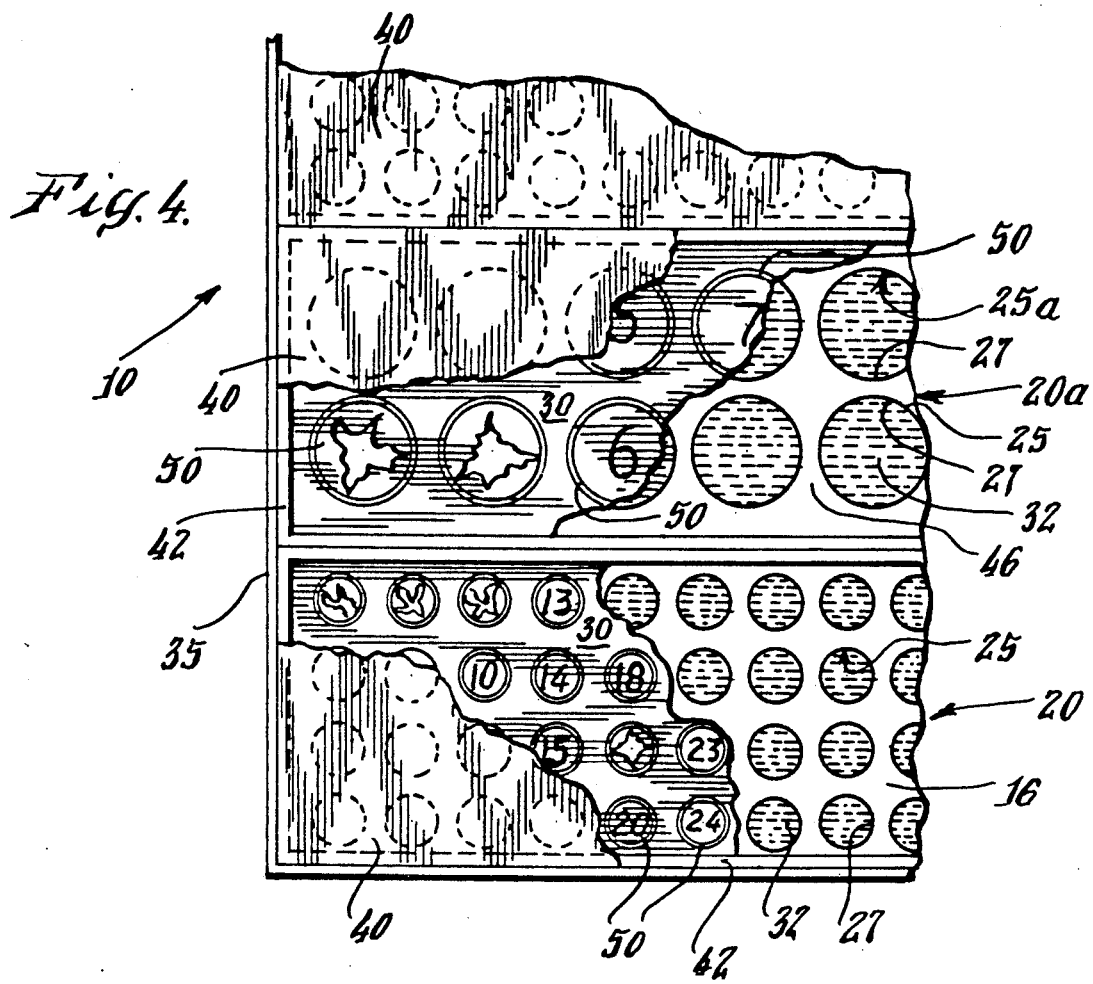
FIG. 4 is a top view, partially cut away, of the sharps disposal system of FIG. 1.

A disposal system 10 for biologically contaminated sharp instruments, such as syringes, generally comprises a container 20 having a plurality of elongated, aligned receptacles 25 therein. The receptacles 25 each respectively define an entry opening 27 which is covered by a rupturable seal 30. The receptacles 25 contain a liquid 32, the liquid 32 being curable to a hardened condition upon breaking of the seal 30 and exposure of the liquid to the air. Therefore, a sharp instrument, such as syringe 15, may be inserted through the foil seal 30 and immersed in the liquid 32 within a receptacle, whereafter the liquid hardens to encase the syringe.

With reference to FIGS. 1, 3 and 4, the sharps disposal system 10 further comprises a rack 35 for mounting several of the containers on a wall at the desired location in a hospital or other medical care facility. More particularly, the rack 35 is sized to mount a total of three containers 20 and 20a, container 20a being characterized by different sized receptacles 25a. Thus, at least one container 20 and one container 20a are available for use at any given time, and a spare container of either size is placed in the rearward position, in effect, stored for ready availability upon filling of the other container.

Figure 5:
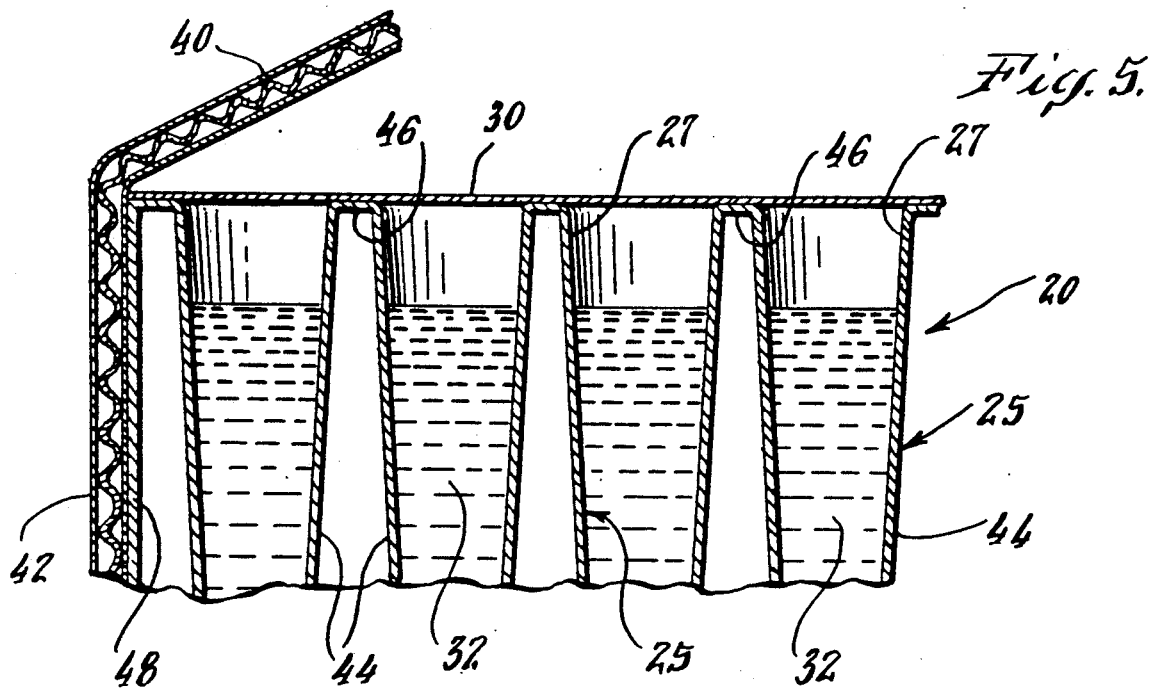
FIG. 5 is an enlarged segmental cross sectional view of one of the the containers of the sharps disposal system of FIG. 1.

The container 20 is generally rectangular and comprises side walls, a bottom wall and a lid 40 pivotally attached to one of the side walls 42. The walls of the container are fabricated of corrugated cardboard or the like, with a waxed waterproof surface. As best seen in FIGS. 2-5, the receptacles 25, 25a each comprise a puncture resistant casing 44. When the disposal system is intended for syringes, scalpels, and similar elongated tools, the receptacle casings 44 are elongated and may be tapered toward the lower end, i.e. having the shape of a truncated cone. The casings 44 are fabricated of a puncture resistant material, such as a polyethylene, and rows and columns of the casings 44 are integrally fabricated by molding them together. As discussed above, each of the receptacles 25 defines an entry opening 27, and the polyethylene casing material integrally forms a top panel 46 which extends between the entry openings of the respective receptacles. The top panel 46 includes a depending peripheral wall 48, as best seen in FIG. 5, for joining the top panel with the container side walls and thereby positioning and supporting the receptacles within the container 20.

The seal 30 is adhered to the top panel 46 and extends across the entry openings of the individual receptacles. The seal 30 is a foil sheet which is readily breakable in order to insert a contaminated instrument into one of the receptacles. The seal includes an indication of the location of the receptacle openings, preferably in the form of contrasting color areas, such as annular bands 50 best seen in FIG. 4. The foil seal also includes a printed number positioned over the entry opening to each receptacle, the numbers sequentially increasing and indicating the total number of receptacles per container. The numbers are also best seen in FIG. 4.

The lid 40 of the container 20 is pivotable to be positioned over the foil seal 30, in order to protect the seal prior to use of the container.

The receptacles are filled with a liquid 32 which is curable upon rupture of the seal 30. The liquid 32 is preferably viscous prior to curing to a hardenable state, so that it does not splash or spill out of the receptacle easily. A suitable liquid is vinyl coating solution manufactured by Sterling Engineered Products, Cleveland, Ohio, under its product number XL-8. This material remains liquid until contacted by air, and cures within a matter of a few minutes to a hardened state. Fast curing plastisols may also be suitable for use as the receptacle liquid, as are any other materials which are of at least low toxicity (they will be touched as the sharp is inserted) and quick curing. Further, the liquid may be one curable by introduction of a catalyst or other substance, which may be introduced as the seal is broken and the instrument inserted.

The liquid 32 includes a germicidal additive, such as formalin, in order that the liquid kill or inhibit the growth of any biological contaminates on instruments inserted therein.

The container 20a is similar to the container 20 in all respects except for the size of the receptacles. The container 20a has larger receptacles 25a for accepting larger instruments. In the embodiments shown, the receptacles of container 20 have entry openings which are one inch in diameter, the receptacles have a depth of ten inches, and taper to one half inch in diameter at the distal end. The receptacles of container 20a have entry openings one and three quarters inch in diameter, a depth of twelve inches and taper to three quarters inch in diameter at their distal ends. It will be appreciated that the receptacles may be made in any desired size or configuration, as required for the particular instruments to be accommodated.

The wall bracket 35 is mounted at a location convenient to the use of sharps instruments. The lids of the two containers 20 and 20a are folded back, exposing the foil seals and the indicia thereon indicating the entry openings to the receptacles. The third container, which is shown to be container 20, but may be one of the containers 20a, is in the position closest the wall, stored for use when either of the other two containers are full.

Upon completing a procedure using sharp instruments, such syringes 15, the medical personnel inserts the used syringe 15 through the foil seal 30 and into one of the receptacles, where it is immersed in liquid 32 as best seen in FIG. 3. It is desired and anticipated that the instrument will be inserted into the lowest numbered receptacle which has not been used, whereby merely glancing at the container at any time provides an accurate count of the number of instruments disposed of therein. This is illustrated in FIG. 4, wherein receptacles Nos. 1-4 of container 20a have been used, and receptacles 1-9 of container 20 have been used, as indicated by the ruptured seals.

The foil seal 30 is ruptured as syringe 15 is inserted therethrough, exposing the liquid 32 within the receptacle to the air. The syringe is, of course, pushed down into the liquid and immersed therein, and the liquid then cures into a hardened condition surrounding the syringe, as best seen in FIG. 3. This completely shields the syringe from contact, and prevents the syringe from being withdrawn for unauthorized use, such as by a drug addict. The germicide in the liquid also prevents the contaminants from growing in the liquid as well.

When a container 20 is full (or sooner if desired), it may be removed from the bracket 35 and be replaced there by a fresh container. The full container may be autoclaved, if desired, to raise its temperature to a point ensuring the destruction of microorganisms. At elevated temperatures, the plastics involved, including the casings and the plastic portions of syringes or other instruments, may soften and collapse, but this does not cause exposure of the instruments. The container may then be buried. Alternatively, the container may be disposed of by incineration.

The sharps disposal system according to the invention herein and the preferred embodiment system 10 described above provides for total control, protection and accountability with respect to instruments from the time of their us to their disposal. Yet, the system is easy to use and of modest cost, particularly in view of the total control, protection and accountability it provides. Accordingly, the sharps disposal system disclosed herein admirably achieves the objects of this invention. It will be appreciated that the preferred embodiment is illustrative only and that various changes may be made by those skilled in the art without departing from the spirit and scope of the invention, which is limited only by the following claims.

I claim:

1. A disposal system for contaminated sharp instruments such as syringes, comprising at least one receptacle having a puncture resistant casing defining an entry opening, a rupturable seal deployed over the entry opening, and a curable liquid contained within the casing and seal, said liquid being curable to a hardened state upon rupture of the seal, whereby a sharp instrument may be pushed through the seal into the liquid within the receptacle and the liquid then hardens about the sharp instrument.

2. A disposal system as defined in claim 1 wherein the liquid is viscous and resists splashing and spilling as the instrument is inserted therein.

3. A disposal system as defined in claim 2 wherein the liquid is vinyl coating solution.

4. A disposal system as defined in claim 1 wherein the liquid includes means to inhibit the growth of biological contaminants.

5. A disposal system as defined in claim 1 and further comprising a plurality of receptacles having their puncture resistant casings integrally formed and connected.

6. A disposal system as defined in claim 5 wherein the entry openings to the plurality of receptacles are in a common plane and the area between the entry openings is a top panel integrally connecting the plurality of receptacles.

7. A disposal system as defined in claim 6 wherein the rupturable seal is affixed to the top panel and extends over the entry openings to the plurality of receptacles.

8. A disposal system as defined in claim 7 wherein the rupturable seal includes a metal foil.

9. A disposal system as defined in claim 7 wherein the rupturable seal is provided with indicia indicating the respective locations of the entry openings to the plurality of receptacles.

10. A disposal system as defined in claim 9 wherein the indicia indicating the location of the entry openings to the receptacles include sequentially ascending numbers, whereby the number of receptacles having an instrument disposed of therein is readily ascertainable.

11. A disposal system as defined in claim 9 wherein the indicia include contrasting color areas positioned to indicate the locations of entry openings.

12. A disposal system as defined in claim 5 wherein the puncture resistant casing is in the shape of a truncated cone defining a circular entry hole at its larger end.

13. A disposal system as defined in claim 5 wherein at least some of the receptacle casings have a circular entry opening having a diameter of approximately one inch and have a depth of approximately ten inches.

14. A disposal system as defined in claim 5 wherein at least some of the receptacles have an entry opening having a diameter of approximately one and three quarters inches and a depth of approximately twelve inches.

15. A disposal system as defined in claim 5 wherein the integrally formed puncture resistant casings mounted within a container.

16. A disposal system as defined in claim 15 wherein the container includes a lid pivotal to a position covering and protecting the rupturable seal.

17. A disposal system as defined in claim 15 wherein the container is a right rectangular container.

18. A disposal system as defined in claim 1 wherein the rupturable seal includes a metal foil.

19. A disposal system as defined in claim 1 wherein a plurality of receptacles are deployed in a container.

20. A disposal system as defined in claim 19 wherein the entry openings to the plurality of receptacles are in one plane.

21. A disposal system as defined in claim 20 wherein the rupturable seal for the receptacles is a metal foil sheet deployed over the plurality of entry openings.

22. A method of disposing of a sharp instrument comprising the steps of rupturing a seal covering a liquid curable upon exposure to air, immersing the instrument in the liquid and permitting the liquid to cure.

23. A method of disposing of a contaminated sharp instrument comprising the steps of:
  A) providing a receptacle having a casing defining an entry opening, an air-curable liquid within the casing and a rupturable seal over the entry opening;
  B) breaking the rupturable seal;
  C) immersing the sharp instrument in the liquid; and
  D) exposing the liquid to the air for curing.

24. A disposal system as defined in claim 19 wherein the rupturable seals deployed over the entry openings respectively include sequentially ascending numbers, whereby the number of receptacles having an instrument disposed of therein is readily ascertainable.

* * * * *